United States Patent [19]

Yago

[11] Patent Number: 5,551,436
[45] Date of Patent: Sep. 3, 1996

[54] MEDICAL DIAGNOSIS SYSTEM

[75] Inventor: Akihiko Yago, Tokyo, Japan

[73] Assignee: Hardy Co., Ltd., Tokyo, Japan

[21] Appl. No.: 255,726

[22] Filed: Jun. 7, 1994

[30] Foreign Application Priority Data

Jun. 10, 1993 [JP] Japan ................................ 5-163845

[51] Int. Cl.$^6$ .................................................. A61B 5/02
[52] U.S. Cl. ........................................ 128/670; 128/671
[58] Field of Search ..................................... 128/670, 671

[56] References Cited

U.S. PATENT DOCUMENTS

| 4,053,951 | 10/1977 | Hudspeth et al. | 128/670 |
| 4,232,682 | 11/1980 | Veth | 128/671 |

FOREIGN PATENT DOCUMENTS

| 62-245373A | 10/1987 | Japan . |
| 1-163873A | 6/1989 | Japan . |
| 2-55032A | 2/1990 | Japan . |
| 2-140153A | 5/1990 | Japan . |
| 3-206560A | 9/1991 | Japan . |
| 4-338826A | 11/1992 | Japan . |

*Primary Examiner*—Angela D. Sykes
*Assistant Examiner*—Stephen D. Huang
*Attorney, Agent, or Firm*—Ronald J. Kubovcik

[57] ABSTRACT

A medical diagnosis system includes an input such as a floppy disk drive or a keyboard for inputting data of test items obtained by doctor's consultation, physical examination, and/or test. A microprocessor unit (1) compares the input data with evaluation ranges to determine into which evaluation range the input data falls, (2) compares the evaluation range with condition groups each including one or more condition formulae, thereby generating an evaluation result of sickness or disorder, and (3) provides data of sickness or disorder including type, level, causes, and comments if the condition groups are satisfied, thereby preparing a list of evaluation results. In the event different evaluation results are obtained with respect to a sickness or disorder, the most serious evaluation result for such sickness or disorder is added to the list of evaluation results. An output such as a printer, floppy disk drive, or display monitor displays the evaluation results list in a sentence format.

6 Claims, 3 Drawing Sheets

MEDICAL DIAGNOSIS SYSTEM

BACKGROUND OF THE INVENTION

1. Field of the Invention

The present invention relates to a medical diagnosis system for use in diagnosis and evaluation in medical treatments and medical examinations.

2. Prior Art

Recently a medical checkup such as a health screening including various kinds of tests such as blood analysis, urine analysis, electrocardiography, X-ray examination, etc. is conducted on a regular basis. Because a number of people usually take several medical tests at a time in a regular medical checkup, doctors have a heavy workload.

For example, a doctor follows procedures comprising the steps of (1) dividing a large number of test results into sets of data for individuals, (2) spreading papers of the test results on a desk to check them, (3) finding out possible problems based on abnormal symptoms in the test results, (4) checking and analyzing all the results of test items relating to such possible problems, (5) preparing diagnostic comments based on his analysis, and (6) adding handwritten diagnostic comments to an examination report. This method called "overall evaluation method" makes a doctor spend more than 10 minutes in average to analyze the medical examination results for each individual.

In addition, this method involves other problems; for example, overall evaluations are not always the same for all doctors analyzing the same data. Also, a doctor does not always give the same overall evaluation based on the same data.

In many medical institutions where regular medical checkups are conducted, computers are utilized for printing the results of diagnosis and overall evaluation on a sheet form called an examination report. However, since the content printed out by a computer is in many cases limited to numerical values and simple doctor's comments, it is rather difficult for a patient or a client to well understand the printed results. When more detailed comments are further required, handwritten comments are usually added to a printed examination report by a doctor. In this case, since handwritten comments are added mostly in a short period of time, they are sometimes illegible and insufficient.

Under these circumstances, attempts have recently been made to introduce a medical diagnosis system employing an expert system technology in order to ease the doctor's workload. In such an expert system, the know-how of experts is introduced into a computer program and various procedures, mainly diagnostic determination, are conducted by the computer. Specifically, an expert system is composed of preparing groups of complex conditions and describing them by a program language. This kind of a medical diagnosis system provides both medical institutions and patients or clients with benefits such as improved accuracy and efficiency of diagnosis and medical examination.

However, since medical data obtained by doctor's consultation, physical examination and testing in medical care have wide varieties in their forms, descriptions and units, complex computer processing procedures are required to process each of the medical data which taking into consideration the contents of the data. Therefore, large numbers of processes are needed to develop such a program mainly composed of condition groups, and a computer must process a large amount of data during the execution of the program. Thus, a medical diagnosis system has not been achieved unless using a large-scaled computer system of an office computer level or higher due to its development cost and processing capacity.

Under these circumstances, various other medical diagnosis systems have been proposed. For example, JP-A-1-163873 discloses a diagnosis-assisting system providing a diagnostic information on sickness or disorder by comparing input information about patient's symptoms with the content of a rule-type database comprising a cluster of rules described by the phrase of "If . . . , then . . . " and used in the same category, wherein the system includes a means for limiting the candidates of the patient's sickness or disorder to fewer numbers by comparing input data of patient's symptoms with the content of a frame-type database according to the rules of the rule-type database; a sickness or disorder-identifying means for presuming the patient's sickness or disorder by inquiring the symptoms of the limited candidates of sickness or disorder and storing in memory the names of the more limited sickness or disorder and presumption processes; and a means for displaying the names of the sickness or disorder and the presumption processes in a predetermined order as well as information on the identified sickness or disorder. However, this reference does not disclose the details of the system and the steps of limiting the candidates of sickness or disorder seems rather complicated.

Further, JP-A-2-55032 discloses a diagnosis system using data obtained by examining a patient, wherein the system comprises a means for calculating a disease mode index by nonlinearly transforming plural data, multiplying each transformed value by a predetermined coefficient and adding the resultant products, a knowledge base for presuming the extent of sickness or disorder, and a means for presuming the extent of sickness or disorder by using the disease mode index determined by the above disease mode index-calculating means and the knowledge retrieved from the knowledge base. For example, a disease mode index (DMI) of diabetes is obtained by non-linearly transforming the measured blood sugar levels (at fasting, after 1 hour, after 2 hours) into the ratings $S_n$ and calculating the following formula:

$$DMI = W_1 \times S_1 \text{ (at fasting)} + W_2 \times S_2 \text{ (1 h)} + W_3 \times S_3 \text{ (2 h)},$$

wherein $W_1$=0.4 (weight coefficient at fasting), $W_2$=0.25 (weight coefficient after 1 hour) and $W_3$=0.35 (weight coefficient after 2 hours). However, this system is effective only in diagnosis of limited sickness or disorder, and the formula of DMI would be quite complicated in the case of conducting diagnosis for a wide range of possible sickness or disorder as in a regular medical checkup.

SUMMARY OF THE INVENTION

As a result of intense researches in view of the above problems in prior art, the present inventor has found that a remarkably accurate medical diagnosis can be attained by evaluating data obtained by doctor's consultation, physical examination, or a test which doctors usually employ in medical examinations or regular medical checkups, and adopting more serious evaluation results when plural evaluation results are obtained with respect to the same sickness or disorder. The present inventor has further found that a diagnosis system can be miniaturized by employing the above diagnosis method. The present invention has been accomplished based on these findings.

Thus, the medical diagnosis system of the present invention comprises (a) an input means for inputting data of test items obtained by doctor's consultation, physical examination and/or test, (b) an evaluation range-determining means for determining under which evaluation range among a predetermined number of evaluation ranges each of the input data falls, (c) a condition group-determining means for determining which condition groups the input data satisfy by comparing the evaluation ranges of one or more test items relating to each sickness or disorder with predetermined levels, (d) an evaluation engine means for preparing an evaluation result list if each of the condition groups has been checked, more serious evaluation results being written in the list when different evaluation results are obtained with respect to the same sickness or disorder, and (e) an output means for outputting the content of the evaluation result list.

In the more preferred embodiment of the present invention, the medical diagnosis system comprises (a) an input means for inputting data of test items obtained by doctor's consultation, physical examination and/or test, (b) a first memory means for storing evaluation range data prepared by classifying possible values of each test item into a predetermined number of evaluation ranges, (c) an evaluation range-determining means for determining the evaluation range under which each of the input data falls by comparing the input data with the evaluation range data retrieved from the first memory means, (d) a second memory means for storing condition groups in which the evaluation ranges of one or more test items relating to each sickness or disorder are compared with predetermined levels, (e) a condition group-determining means for determining whether the evaluation range of each of the input data satisfies the condition groups retrieved from the second memory means, (f) a third memory means for storing data of findings/tendency, evaluation levels and causes of sickness or disorder and comments, which are to be output as evaluation results if each of the condition groups has been checked, (g) an evaluation engine means for preparing an evaluation result list by using the data of findings/tendency, evaluation levels and causes of sickness or disorder and comments which are retrieved from the third memory means, more serious evaluation results being written in the list when different evaluation results are obtained with respect to the same sickness or disorder; and (h) an output means for outputting the content of the evaluation result list in a usual sentence format.

DETAILED DESCRIPTION OF THE PREFERRED EMBODIMENTS

The present invention will be described in more detail referring to the drawings.

Figure 1:
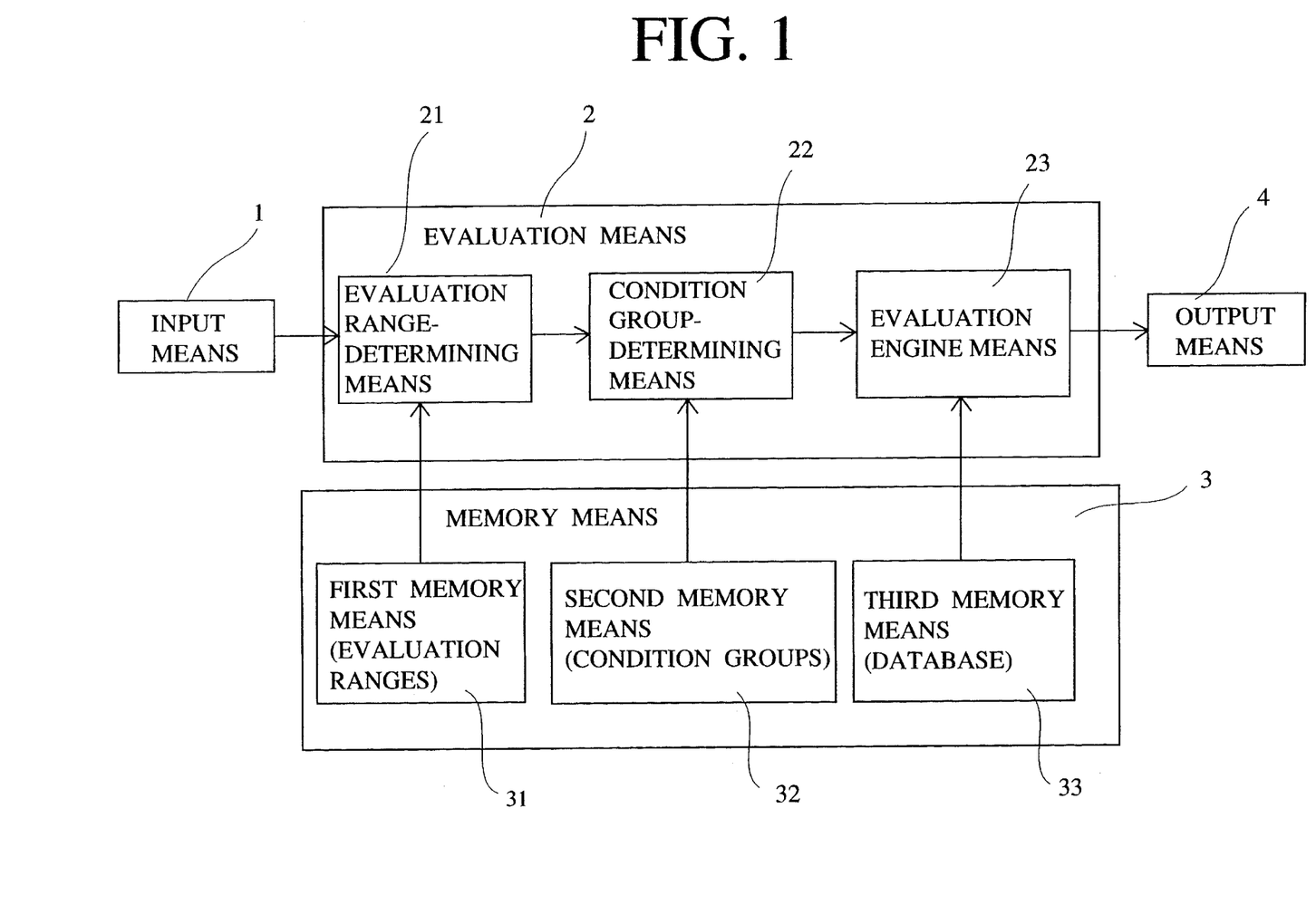
FIG. 1 is a block diagram of the medical diagnosis system according to an embodiment of the present invention.

FIG. 1 is a block diagram of the medical diagnosis system according to an embodiment of the present invention. The medical diagnosis system includes an input means 1 for inputting the data of doctor's consultation, physical examination and test, an evaluation means 2 for diagnosing the symptom of a patient or client based on the input data of doctor's consultation, physical examination and test, a memory means 3 and an output means 4 for outputting the results of diagnosis. The evaluation means 2 includes an evaluation range-determining means 21, a condition group-determining means 22 and an evaluation engine means 23. The memory means 3 includes a first memory means 31 for storing the evaluation ranges, a second memory means 32 for storing the condition groups and a third memory means 33 for storing database necessary for expressing the evaluation results (evaluation levels, findings/tendency, causes, comments, classifications) obtained from the condition group-determining means 22. Incidentally, the memory means 3 may store the input data of doctor's consultation, physical examination and test.

The medical diagnosis system may be constituted by a personal computer. In this case, a floppy disk drive, a mark sheet reader, a keyboard, etc. may be used as the input means 1, a microprocessor unit as the evaluation means 2, RAM, a hard disk, a magneto-optical disk, etc. as the memory means 3, and a printer, a floppy disk drive and/or a display as the output means 4.

[1] Evaluation Range-Determining Means

The evaluation range-determining means 21 determines the evaluation range under which each of the input data of doctor's consultation, physical examination and test falls by comparing the data with the evaluation range table retrieved from the first memory means 1. The evaluation range table includes a predetermined number of classified evaluation ranges in all the test items. Evaluation ranges may be assigned 0, positive integers or negative integers, assuming that "0" represents a normal state, and they are assigned negative or positive integers of larger absolute values if they have higher degrees of abnormality. For example, a certain test item is classified into evaluation ranges of −4, −3, −2, −1, 0, +1, +2, +3 and +4. In this example, the classification gives nine ranges, but the classification is not limited to such ranges. In addition, there is no need to classify all test items into the same number of ranges. The evaluation range may be modified, if desired, depending on sex, age, human race, etc. The classification results of the evaluation ranges are stored in the memory means 3.

The evaluation ranges for some test items are shown in the following Table 1.

TABLE 1

| | Evaluation Ranges | | | | |
| --- | --- | --- | --- | --- | --- |
| Test Item | −4 | −3 | −2 | −1 | 0 |
| Monocyte | — | — | — | $1.0 < n$ | $1.0 \leq n \leq 6.0$ |
| Fasting Blood Sugar Level | — | $n < 50$ | $50 \leq n < 60$ | $60 \leq n < 70$ | $70 \leq n \leq 110$ |

TABLE 1-continued

| | | | | | |
|---|---|---|---|---|---|
| Blood Sugar Level (After 1 hour) | — | n<80 | 80≦n<95 | 95≦n<110 | 110≦n≦160 |
| GOT | — | — | — | n<10 | 10≦n≦40 |
| X-Ray Gastric Diverticulum | — | — | — | — | No |
| Smoking (Cigarettes/Day) | — | — | — | — | No |

| Test Item | Evaluation Ranges | | | |
|---|---|---|---|---|
| | +1 | +2 | +3 | +4 |
| Monocyte | 6.0<n≦7.0 | 7.0<n≦8.0 | 8.0<n≦10.0 | 10.0<n |
| Fasting Blood Sugar Level | 110<n≦120 | 120<n≦140 | 140<n | — |
| Blood Sugar Level (After 1 hour) | 160<n≦170 | 170<n≦200 | 200<n | — |
| GOT | 40<n≦100 | 100<n≦250 | 250<n | — |
| X-Ray Gastric Diverticulum | suspected | certain | — | — |
| Smoking (Cigarettes/Day) | 1–10 | 11–20 | 21≦ | — |

The evaluation range tables are prepared for all of the test items without filling table cells for the evaluation ranges having no possible values.

The standardization of the values of test items into (2n+1) levels from −n to +n makes it quite easy to determine whether or not the values of test items meet the condition groups each consisting of a combination of some evaluation range formulae.

[2] Condition Group-Determining Means (1) Condition group

Each test item comprises an assembly of the condition groups each consisting of an evaluation range condition (formula) of the above particular test item combined with the evaluation range formulae of other closely related test items, and each of the condition groups is determined on whether or not it is satisfied. In an ordinary diagnosis, a doctor first checks a particular test item. When the doctor finds abnormality in the data, he further checks the data of other related test items, and then makes an overall evaluation on whether or not sickness or disorder is present. The combination of the test items to be checked varies depending on sickness or disorder.

The condition groups of the present invention, which are prepared based on a simulation of a diagnosis method employed by a doctor, determine whether or not the test results satisfy all the evaluation range formulae of a plurality of test items.

The condition groups stored in the second memory means 32 are shown in Table 2, taking monocyte for example as a test item.

Table 2

(a) (Monocyte≦−1) and (Hb≦−2).

(b) (Monocyte≦−1) and (other than the above)

(c) (Monocyte=+1) and {(CRP≧+2) or (erythrocyte sedimentation ratio≧+2) or (pyrexia=+1)}.

(d) (Monocyte=+1) and (other than the above).

(e) (Monocyte≧+2) and {at least two of (CRP≧+2) or (erythrocyte sedimentation ratio≧+2) or (pyrexia=+1) or (sputum≧+1) or (cough≧+1) or (X-P.abnormal shadow)}.

(f) (Monocyte≧+2) and {(TPHA≧+1) or (slide precipitation test≧+1).

(g) (Monocyte≧+2) and {at least two of (cardiac murmurs) or (pyrexia=+1) or (fatigue≧+1) or (petechial bleeding≧+1)}.

(h) (Monocyte≧+2) and {at least two of (CRP≧+2) or (erythrocyte sedimentation ratio≧+2) or (cardiac murmurs) or (pyrexia=+1) or (sputum≧+1) or (cough≧+1) or (X-P.abnormal shadow) or (fatigue≧+1) or (petechial bleeding≧+1)}.

(i) (Monocyte≧+2) and {at least two of (GOT≧+2) or (CRP≧+2) or (ZTT≧+2) or (γ-GTP≧+2) or (HBsAg≧+1)}.

(j) (Monocyte≧+2) and [at least two of {(arthralgia≧+2) or (arthrocele≧+2)} or (RA≧+1) or (morning stiff hand≧+1) or (erythrocyte sedimentation ratio≧+2) or (CRP≧+2) or (leukocyte≧+2) or (Hb≧+2)].

(k) (Monocyte≧+2) and [{(X-P.hilar lymphadenopathy.right)and (X-P.hilar lymphadenopathy.left)} or (ultra sound.abdominal lymphadenopathy) or (lymphadenopathy≧+1)].

(m) (Monocyte≧+2) and {(hypogastric pain) or (diarrhea)} and {at least two of (A/G≦−2) or (ZTT≧+2) or (total protein≧+1) or (erythrocyte sedimentation ratio≧+2) or (CRP≧+2) or (leukocyte≧+2) or (bloody stool≧+1)}.

(n) (Monocyte≧+2) and [at least two of (leukocyte≦−2) or (Hb≦−2) or (total protein≧+2) or (raynaud symptom≧+1) or (arthralgia≧+1) or {(TPHA=OK) and (slide precipitation test≧+1)}].

(p) (Monocyte≧+2) and (other than the above).

Note

Hb: Hemoglobin (blood cell count).

CRP: C-Reactive protein (serum assay).

RA: RA test (serum assay).

HBsAg: HBs antibody (RPHA) (serum assay).

TPHA: (Syphilis).

Slide precipitation test: (syphilis).

ZTT: Kunkel (liver function).

A/G: Albumin/globulin ratio (liver function).

Other than the above: Evaluation range is not included in the range of the just preceding condition group with respect to the same test item as that of the just preceding condition group.

(2) Determination of the condition group

In determining whether or not each condition group is met, every evaluation range formula for the test item included in the condition group is determined one by one. For example, in the case of the above condition group (e), the determination is made in the following order:

(i) Is the formula of (monocyte$\geq$+2) satisfied?

(ii) Is at least two of the formulae of (CRP$\geq$+2), (erythrocyte sedimentation ratio$\geq$+2), (pyrexia=+1), (sputum$\geq$+1), (cough$\geq$+1) and (X-P.abnormal shadow) satisfied?

"1" is assigned when each evaluation range formula is satisfied, while "0" is assigned when it is not satisfied. When an evaluation range formula is satisfied, the integer increment variable P increases by a predetermined integer. As a result, it is possible to compare the integer increment variable P with the number given in the evaluation range condition (formula) to determine whether the condition group is satisfied or not. For example, in the case of the above condition group (e), P=P+10 if the condition (i) of (monocyte$\geq$+2) is satisfied, and P=P+1 if the condition (ii) is also satisfied. Since at least two evaluation ranges should be satisfied in the condition (ii), if the integer increment variable P satisfies the equation, $P \geq 1 \times 10 + 2 \times 1$, it is confirmed that the condition group (e) is satisfied.

The determination process for the following condition group which is similar to the condition group (j) is shown in Table 3 below as a more complicated example. Whether or not the condition group is met is determined by the comparison of the incrementally increasing values of the integer increment variable P with the predetermined value.

Table 3

Condition Group
(Monocyte$\geq$+2) and {(arthralgia$\geq$+2) or (arthrocele$\geq$+2)} and {at least two of (RA$\geq$+1) or (erythrocyte sedimentation ratio$\geq$+2) or (Hb$\geq$+1) or (CRP$\geq$+2)}.

Preliminary Processing (1) P=0.

(2) If monocyte$\geq$+2, P=P+100.

(3) If arthralgia$\geq$+2, P=P+10.

(4) If arthrocele$\geq$+2, P=P+10.

(5) If RA$\geq$+1, P=P+1.

(6) If erythrocyte sedimentation ratio$\geq$+2, P=P+1.

(7) If Hb$\geq$+1, P=P+1.

(8) If CRP$\geq$+2, P=P+1.

Determining if Condition Group is satisfied
$P \geq 112$.

In the examples described above, only one integer increment variable is used as a subject of increment. However, since a plurality of condition groups are present, a plurality of integer increment variables such as P1, P2, . . . , Pn are necessary in order to determine all the condition groups.

[3] Evaluation Engine Means (1) Database for expressing evaluation results

The data of findings/tendency and causes of sickness or disorder and comments, which are used to fill the evaluation result list, are retrieved from the database stored in the third memory means 33 in the memory means 3 in accordance with the determination results of the condition groups. This is performed by the evaluation engine means 23. Examples of the findings/tendency of sickness or disorder are shown in Table 4 below.

TABLE 4

| Number | Findings/Tendency |
|---|---|
| 001 | Hemolysis |
| 002 | Chylomicron |
| 003 | Positive atypical antibody reaction |
| 004 | A few positive Rh minus reaction |
| 005 | Decrease in erythrocyte sedimentation ratio (1 hour) |
| . | . |
| . | . |
| . | . |

Examples of the causes of sickness or disorder are shown in Table 5 below.

TABLE 5

| Number | Causes |
|---|---|
| 01 | Hypervolemia |
| 02 | Cold syndrome |
| 03 | Gingivitis |
| 04 | Pyoderma |
| 05 | Anemia |
| 06 | Nephrotic syndrome |
| 07 | Chronic rheumatoid arthritis |
| . | . |
| . | . |
| . | . |

Examples of the comments on sickness or disorder are shown in Table 6 below.

TABLE 6

| Number | Comments |
|---|---|
| 001 | Glucose tolerance test is required. |
| 002 | Improvement of living conditions is required. |
| 003 | Diagnosis by an internist is required. |
| 004 | Examination of abnormal hemoglobin is required. |
| 005 | Fractionation of plasma protein is required. |
| 006 | Examination on hemolysis is required. |
| 007 | Examination of hepatitis C virus antibody is required. |
| . | . |
| . | . |
| . | . |

It should be noted that the findings/tendency, causes and comments in the above Tables 4–6 are only part of them, and that there are many other findings/tendency, causes and comments than those shown in the above tables.

(2) Preparation of evaluation result list

Table 7 exemplifies an evaluation result list showing the evaluation results obtained by using the condition groups of Table 2, referring to the list of the findings/tendency, causes and comments.

TABLE 7

| Condition Group | Sickness or Disorder | | | |
|---|---|---|---|---|
| | Findings/tendency | Level | Causes | Comments |
| (a) | Decreased Monocyte | E | Pernicious Anemia | Monocyte is phagocytotic leukocyte important for immuno-reaction |
| (b) | Decreased Monocyte | B | — | |
| (c) | Increased Monocyte | D | Some Infection | |
| (d) | Increased Monocyte | B | — | |
| (e) | Increased Monocyte | E | Some Infection | |
| (f) | Increased Monocyte | E | Chronic Infectious Disease | |
| (g) | Increased Monocyte | E | Chronic Infectious Disease | |
| (h) | Increased Monocyte | D | Some Infection | |
| (i) | Increased Monocyte | C2 | Hepatocyte Disorder | |
| (j) | Increased Monocyte | E | Chronic Rheumatoid Arthritis | |
| (k) | Increased Monocyte | E | Sarcoidosis | |
| (m) | Increased Monocyte | E | Colitis | |
| (n) | Increased Monocyte | E | Some Connective Tissue Disorder | |
| (p) | Increased Monocyte | D | Some Infection | |

Table 7 is an evaluation result list concerning the test item of monocyte. However, in an actual diagnosis, since medical examination is conducted in a wide variety of test items, an evaluation result list refers to all possible sickness or disorder. For example, part of the evaluation result list is shown in Table 8.

TABLE 8

| Test Item | Findings/tendency | Classification | Level |
|---|---|---|---|
| Monocyte | Increased Monocyte | 12 | E |
| Systolic Blood Pressure | Elevated Systolic Blood Pressure | 2 | E |
| Fasting Blood Sugar Level, HbA$_{1c}$ | Diabetes | 13 | C2 |
| Total Protein · A/G Ratio | Abnormal Plasma Protein Fractionation | 20 | E |
| Uric Acid | Hypouricemia | 15 | D |

| Causes | Comments |
|---|---|
| Chronic Rheumatoid Arthritis | Take close examination. |
| Obesity, Lack of Exercise | Try to reduce your weight and have moderate exercise. |
| Obesity/Drinking | Do not drink too much. |
| — | Renal calculus may occur. |
| — | Plasma protein fractionation is required. |

All the sickness or disorder is classified into 1–20 groups by its sites and major sickness or disorder. A certain sickness or disorder may be classified into different groups. For example, "elevated ATT value" may be classified into "connective tissue disorder" or "other metabolic disorder." The classification of the evaluation on each "sickness or disorder" into 1–20 groups is called "evaluation by sites." When a plurality of evaluations appear at the same site, the most serious one is adopted.

Since there are plural other test items which are to be combined with each test item, each test item has a plurality of condition groups. The results (findings/tendency, evaluation levels and causes of sickness or disorder and comments) derived from the evaluation of some condition groups are sometimes duplicated, and therefore, the results have to be arranged in order to avoid contradiction.

This arrangement is performed by the evaluation engine means. When an evaluation result (findings/tendency, evaluation level and cause of sickness or disorder and comment) is obtained, the result is written in the evaluation result list. If the evaluation result for the same sickness or disorder is already present, the evaluation levels of both evaluation results are compared. If the evaluation level already existing in the list is more serious than that of the new one, the new evaluation result is not added. On the other hand, if the evaluation level of the new evaluation result is more serious than that of the evaluation result already written in the list, then the evaluation result is substituted by the new one.

Since the evaluation results are written in the evaluation result list in such a way as mentioned above, there is no duplication in the diagnosis result matrix although a plurality of condition groups are applied to one sickness or disorder.

Incidentally, only computer codes for findings/tendency, evaluation levels and causes of sickness or disorder and comments are actually written in the evaluation result list, and the sentences present in Table 8 are produced from the words and phrases retrieved from the database stored in the third memory means 33.

(3) Preparation of evaluation report

After determination is made on whether or not all the condition groups are met and the evaluation results are subsequently written in the evaluation result list, a complete comment sentence is produced for each sickness or disorder by synthesizing the comment words or phrases and the conjunctive words or phrases both of which are extracted from the comment master stored in the third memory means 33.

The above procedure will be described below, specifically taking the row of diabetes in Table 8 for example. By assigning comment words, "Since . . . is found, please take examination again within one month." to the evaluation level "C2", an example for complete comments is, "Since the sign of diabetes is found from the fasting blood sugar level.$HbA_{1c}$, please take examination again within one month. It may be caused by obesity and drinking. Please do not drink to excess."

When no abnormality is found in all the test items, a sentence to be printed in the column for findings/tendency is, for example, "No abnormal symptoms have been found from today's examination."

The diagnosis results may be output in the form of a matrix in which all the sickness or disorder is classified into 20 groups and sickness or disorder in each group is classified into evaluation levels (A, B, C, D, E and F), with symbols such as o, etc. described in appropriate portions of the matrix. An example of such a matrix is partially shown in Table 9 below.

TABLE 9

| Level | 1 Circulatory Organs | 2 Hypertension | 3 Respiratory Organs | 4 Digestive Organs | 5 Liver | . . . |
|---|---|---|---|---|---|---|
| A | ⊙ | | | | | |
| B | | | O | | | |
| C | | | | | | |
| D | | | | | | |
| E | | | | X | X | |
| F | | X | | | | |

Note:
A: No abnormality.
B: A little abnormal symptom with no need to worry.
C: Observation should be continued.
D: Examination should be taken again.
E: Close examination is required.
F: Treatment should be started.

[4] Output Means

The findings/tendency, causes and comments obtained by the process described above are output in a recording medium desired by a patient or client in the form of a complete sentence through the output means 4 (printer, floppy disk drive, etc.) referred to in FIG. 1.

[5] Flow Chart of the System

Figure 2:
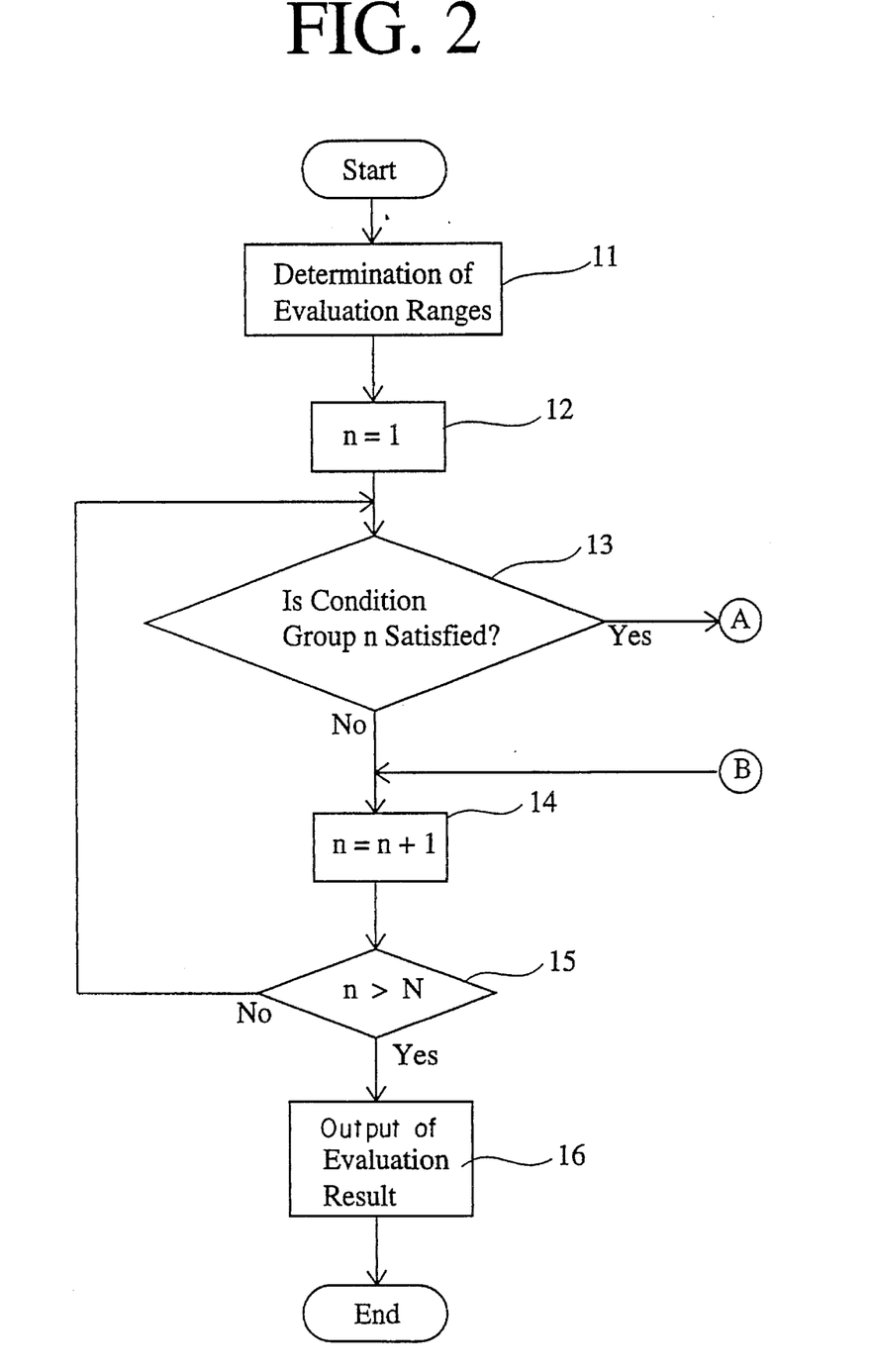
FIG. 2 is a flow chart illustrative of operating the medical diagnosis system according to an embodiment of the present invention.
Figure 3:
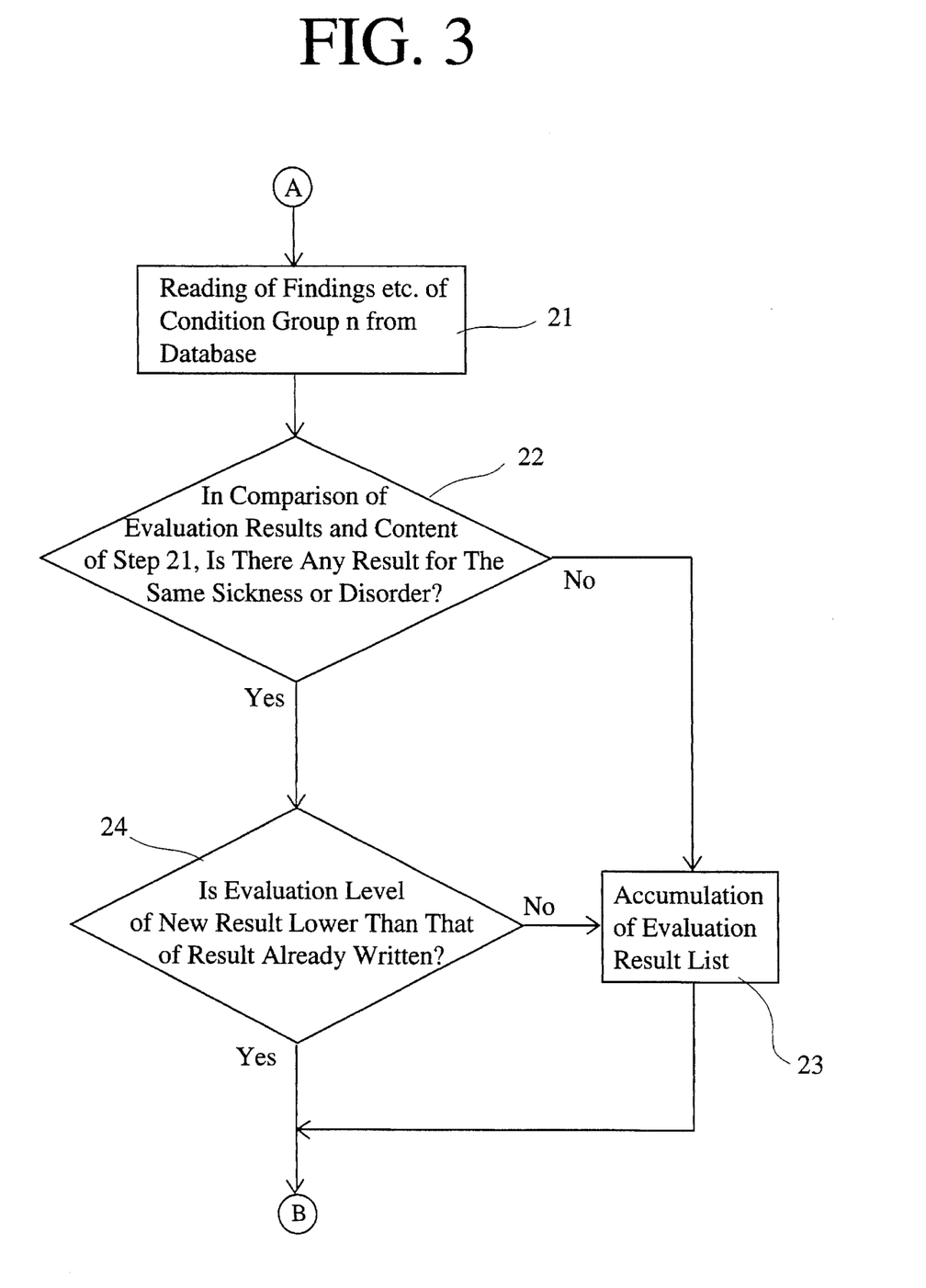
FIG. 3 is a flow chart illustrative of operating the medical diagnosis system according to an embodiment of the present invention.

FIG. 2 is a flow chart illustrative of operating the medical diagnosis system of the present invention. First, the evaluation range is determined (step 11), and "n" is assumed to be 1 (step 12). If it is assumed that the condition groups stored in the second memory means 32 consist of condition group 1, condition group 2, . . . , and condition group N, the condition group 1 is first determined by the condition group-determining means 22 on whether or not it is satisfied (step 13). If the result is YES, then the system goes into A. On the other hand, if the result is NO, B referred to in FIG. 3 is read and the calculation of n=n+1 is done (step 14). The numerical value of "n" is determined on whether or not it is larger than N (step 15). If the result is NO, the system returns to step 13, and the determination of condition group 2 is carried out. In this way, the determination is conducted until reaching n=N. After "n" reaches N, "n" becomes N+1, satisfying n≧N in step 15. Then, the result becomes YES, outputting the evaluation result (step 16).

As shown in FIG. 3, when the system goes to A, the evaluation result (findings/tendency, cause and comment) of the condition group "n" is prepared using data retrieved from the database stored in the third memory means 33 (step 21). Next, determination is conducted on whether or not the evaluation result is already written for the same sickness or disorder in the evaluation result list (step 22). If not already written, the evaluation result is accumulated (written) in the evaluation result list (step 23). On the other hand, if already written, determination is conducted on whether or not the evaluation level of the already written evaluation result is less serious than that of the new evaluation result (step 24). If the evaluation level of the evaluation result already written in the list is less serious than that of the new evaluation result, then the evaluation result already written is deleted by overwriting the new evaluation result in the evaluation result list (step 23). In other words, the new evaluation result is written over the evaluation result already recorded. On the other hand, if the evaluation level of the evaluation result already written in the list is more serious than that of the new evaluation result, the new result is ignored (not written).

After filling the evaluation result list to the nth condition group, determination is conducted on the (n+1)th condition group (step 13). This procedure is repeated until reaching n=N. In accordance with the flow chart, since determination is made on all the condition groups 1, 2, . . . , and N, the evaluation results finally obtained cover all the test items.

As described in detail, the medical diagnosis system of the present invention can be operated by supplying the input data of doctor's consultation, physical examination and test, and the diagnosis and evaluation are performed by a computer, thereby ensuring a high accuracy and efficiency in diagnosis with remarkably reduced doctors' workload. Though the condition group is composed of a combination of the evaluation ranges of related test items, which may lead to multiplication of identified sickness or disorder, causes, comments, etc., such multiplication can be avoided by the evaluation engine means. As a result, the diagnosis can be carried out by a method resembling a doctor's consideration procedure.

Further, the medical diagnosis system of the present invention provides a patient or client with diagnostic examination results in the form of detailed and comprehensible sentences. Moreover, due to simple logic structures and small processing amounts, the medical diagnosis system of the present invention can process the medical data at a sufficient speed even with a small-scaled apparatus such as a personal computer.

What is claimed is:

1. A medical diagnosis system comprising:
   (a) an input means for inputting data of test items obtained by doctor's consultation, physical examination and/or test;
   (b) an evaluation range-determining means for comparing each of said input data with evaluation ranges to determine into which evaluation range each of said input data falls, said evaluation ranges being prepared by classifying possible values of each test item into a predetermined number of groups;
   (c) a condition group-determining means for comparing said evaluation range determined from each of said input data with condition groups each comprising one or more condition formulae, thereby generating an evaluation result of sickness or disorder;
   (d) an evaluation engine means for providing data of sickness or disorder including type, level, causes, and comments if said condition groups are satisfied, thereby preparing a list of evaluation results, wherein in the event different evaluation results are obtained with respect to a sickness or disorder, the most serious evaluation result with respect to such sickness or disorder is added to said list of evaluation results; and (e) an output means for displaying said evaluation result list in a sentence format.

2. The medical diagnosis system according to claim 1, wherein said condition group consists of an evaluation range formula of a particular test item combined with other evaluation range formulae of closely related test items in order to evaluate all the sickness or disorder relating to said particular test item.

3. The medical diagnosis system according to claim 1, wherein said evaluation range for each test item is classified into (2n+1) ranges from −n to +n while assigning 0 to a normal state.

4. The medical diagnosis system according to claim 2, wherein said evaluation range for each test item is classified into (2n+1) ranges from −n to +n while assigning 0 to a normal state.

5. The medical diagnosis system according to claim 1, wherein each condition group comprises one or more evaluation range formulae for comparing the evaluation ranges of one or more related test items with predetermined levels, each of said evaluation range formulae being connected by OR or AND.

6. A medical diagnosis system comprising:

(a) an input means for inputting data of test items obtained by doctor's consultation, physical examination and/or test;

(b) a first memory means for storing evaluation range data prepared by classifying possible values of each test item into (2n+1) ranges from −n to +n while assigning 0 to a normal state;

(c) an evaluation range-determining means for comparing each of said input data with said evaluation ranges retrieved from said first memory means to determine into which evaluation range each of said input data falls;

(d) a second memory means for storing condition groups, each condition group comprising one or more condition formulae for comparing the evaluation ranges of one or more related test items with predetermined levels;

(e) a condition group-determining means for determining whether said evaluation range determined from each of said input data satisfies the condition formulae in said condition groups retrieved from said second memory means, thereby generating an evaluation result of sickness or disorder from said related test items;

(f) a third memory means for storing data of sickness or disorder including type, level, causes, and comments;

(g) an evaluation engine means for retrieving said data of sickness or disorder from said third memory means if said condition groups are satisfied, thereby preparing a list of evaluation results, wherein in the event different evaluation results are obtained with respect to a sickness or disorder, the most serious evaluation result with respect to such sickness or disorder is added to said list of evaluation results; and (h) an output means for displaying said evaluation result list in a sentence format.

* * * * *